United States Patent
Raju et al.

(10) Patent No.: US 11,617,561 B2
(45) Date of Patent: Apr. 4, 2023

(54) ULTRASOUND IMAGING SYSTEM AND METHOD

(71) Applicant: KONINKLIJKE PHILIPS N.V., Eindhoven (NL)

(72) Inventors: Balasundar Iyyavu Raju, North Andover, MA (US); Peter Bingley, Mierlo (NL); Frank Michael Weber, Hamburg (DE); Jonathan Thomas Sutton, Boston, MA (US); Tilman Wekel, Krummesse (DE); Arthur Bouwman, Eindhoven (NL); Erik Korsten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 521 days.

(21) Appl. No.: 16/756,943

(22) PCT Filed: Oct. 16, 2018

(86) PCT No.: PCT/EP2018/078127
§ 371 (c)(1),
(2) Date: Apr. 17, 2020

(87) PCT Pub. No.: WO2019/076839
PCT Pub. Date: Apr. 25, 2019

(65) Prior Publication Data
US 2021/0196228 A1    Jul. 1, 2021

Related U.S. Application Data

(60) Provisional application No. 62/574,360, filed on Oct. 19, 2017.

(30) Foreign Application Priority Data

Dec. 5, 2017    (EP) .................................... 17205318

(51) Int. Cl.
*A61B 8/06* (2006.01)
*G06T 7/33* (2017.01)
(Continued)

(52) U.S. Cl.
CPC .............. *A61B 8/065* (2013.01); *A61B 5/318* (2021.01); *A61B 8/12* (2013.01); *A61B 8/14* (2013.01);
(Continued)

(58) Field of Classification Search
CPC ........... A61B 8/065; A61B 5/318; A61B 8/12; A61B 8/14; A61B 8/466; A61B 8/06;
(Continued)

(56) References Cited

U.S. PATENT DOCUMENTS 4,245,647 A * 1/1981 Randall ................ A61B 5/7242
600/436
5,997,479 A 12/1999 Savord et al.
(Continued)

FOREIGN PATENT DOCUMENTS

WO    2007016369 A2    2/2007

OTHER PUBLICATIONS

International Search Report and Written Opinion, International Application No. PCT/EP2018/078127, dated Jan. 17, 2019.
(Continued)

*Primary Examiner* — Bo Joseph Peng

(57) ABSTRACT

An ultrasound imaging system is for determining stroke volume and/or cardiac output. The imaging system may include a transducer unit for acquiring ultrasound data of a heart of a subject (or an input for receiving the acquired ultrasound data), and a controller. The controller is adapted to implement a two-step procedure, the first step being an initial assessment step, and the second being an imaging step having two possible modes depending upon the outcome of
(Continued)

the assessment. In the initial assessment procedure, it is determined whether regurgitant ventricular flow is present. This is performed using Doppler processing techniques applied to an initial ultrasound data set. If regurgitant flow does not exist, stroke volume is determined using segmentation of 3D ultrasound image data to identify and measure the volume of the left or right ventricle at each of end systole and end-diastole, the difference between them giving a measure of stroke volume. If regurgitant flow does exist, stroke volume is determined using Doppler techniques applied to ultrasound data continuously collected throughout a cardiac cycle.

20 Claims, 3 Drawing Sheets

(51) Int. Cl.
    *A61B 5/318*     (2021.01)
    *A61B 8/12*     (2006.01)
    *A61B 8/14*     (2006.01)
    *A61B 8/00*     (2006.01)

(52) U.S. Cl.
CPC .............. *A61B 8/466* (2013.01); *G06T 7/344* (2017.01); *G06T 2207/10136* (2013.01); *G06T 2207/20121* (2013.01); *G06T 2207/30104* (2013.01)

(58) Field of Classification Search
CPC ....... A61B 8/543; A61B 8/5276; A61B 8/483; A61B 8/488; A61B 8/4405; A61B 8/4472; A61B 8/469; A61B 8/486; A61B 8/0883; G06T 7/344; G06T 2207/10136; G06T 2207/20121; G06T 2207/30104
See application file for complete search history.

(56) References Cited

U.S. PATENT DOCUMENTS

| | | | |
|---|---|---|---|
| 6,013,032 A | 1/2000 | Savord | |
| 6,283,919 B1 | 9/2001 | Roundhill et al. | |
| 6,443,896 B1 | 9/2002 | Detmer | |
| 6,530,885 B1 | 3/2003 | Entrekin et al. | |
| 6,623,432 B2 | 9/2003 | Powers et al. | |
| 8,808,191 B2 | 8/2014 | Hirsh | |
| 2005/0245822 A1 | 11/2005 | Dala-Krishna et al. | |
| 2007/0167809 A1 | 7/2007 | Dala-Krishna | |
| 2008/0058656 A1* | 3/2008 | Costello ............... | A61B 5/1107 600/595 |
| 2011/0208056 A1 | 8/2011 | Datta et al. | |
| 2011/0301466 A1 | 12/2011 | Wang et al. | |
| 2013/0053664 A1 | 2/2013 | Jian et al. | |
| 2013/0132054 A1 | 5/2013 | Sharma et al. | |
| 2013/0278776 A1 | 10/2013 | Guterman et al. | |
| 2013/0303916 A1 | 11/2013 | Aoki et al. | |
| 2015/0078638 A1 | 3/2015 | O.K. Rahmat et al. | |
| 2016/0206292 A1 | 7/2016 | Vezina | |
| 2016/0228190 A1* | 8/2016 | Georgescu ............. | A61B 34/10 |
| 2022/0068481 A1* | 3/2022 | Maessen ................ | G16H 50/20 |

OTHER PUBLICATIONS

Thavendiranathan, P. et al., "Quantitative Assessment of Mitral Regurgitation", JACC: Cardiovascular Imaging, vol. 5, No. 11, Nov. 2012.
Garcia et al., "Echocardiographic assessment of left ventricular function", Journal of Nuclear Cardiol., vol. 13, No. 2, Mar. 2006.
Shiota, T et al., "Real-time Three-dimensional Echocardiography for Determining Right Ventricular Stroke Volume in an Animal Model of Chronic Right Ventricular Volume Overload", Circulation, vol. 97, No. 19, May 1998.
Reuter, D. et al., "Optimizing Fluid therapy in mechanically ventilated patients after cardiac surgery by on-line monitoring of left ventricular stroke volume variations. Comparison with aortic systolic pressure variations", Munich, Germany, Sep. 2001.
Ecabert et al., "Automatic model-based segmentation of the heart in CT images", Oct. 2008.
F. Michard et al., "Relation between Respiratory Changes in Arterial Pulse Pressure and Fluid Responsiveness in Septic Patients with Acute Circulatory Failure," Am. J. Respir. Crit. Care Med., vol. 162, No. 1, pp. 134-138, Jul. 2000.
F. W. Wong, "Pulsus paradoxus in ventilated and non-ventilated patients," Dynamics, vol. 18, No. 3, pp. 16-18, 2007.
D. A. Reuter, T. W. Felbinger, E. Kilger, C. Schmidt, P. Lamm, and A. E. Goetz, "Optimizing fluid therapy in mechanically ventilated patients after cardiac surgery by on-line monitoring of left ventricular stroke volume variations. Comparison with aortic systolic pressure variations," Br. J. Anaesth., vol. 88, No. 1, pp. 124-126, Jan. 2002.
F. Jardin, J. C. Farcot, P. Gueret, J. F. Prost, Y. Ozier, and J. P. Bourdarias, "Cyclic changes in arterial pulse during respiratory support.," Circulation, vol. 68, No. 2, p. 266, Aug. 1983.
B. Tavernier, O. Makhotine, G. Lebuffe, J. Dupont, and P. Scherpereel, "Systolic Pressure Variation as a Guide to Fluid Therapy in Patients with Sepsis-induced Hypotension:," Anesthesiology, vol. 89, No. 6, pp. 1313-1321, Dec. 1998.
H. He, D. Liu, Y. Long, X. Wang, M. Zhao, and X. Lai, "The effect of variable arterial transducer level on the accuracy of pulse contour waveform-derived measurements in critically ill patients," J Clin. Monit. Comput., Aug. 2015.
H. MøLler-SøRensen, K. Graeser, K. L. Hansen, M. Zemtsovski, E. M. Sander, and J. C. Nilsson, "Measurements of cardiac output obtained with transesophageal echocardiography and pulmonary artery thermodilution are not interchangeable: TEE vs thermodilution measurements of CO," Acta Anaesthesiol. Scand., vol. 58, No. 1, pp. 80-88, Jan. 2014.

* cited by examiner

ULTRASOUND IMAGING SYSTEM AND METHOD

This application is the U.S. National Phase application under 35 U.S.C. § 371 of International Application No. PCT/EP2018/078127, filed on 16 Oct. 2018, which claims the benefit of U.S. Provisional Application No. 62/574,360, filed 19 Oct. 2017 and European Application No. 17205318.3, filed 5 Dec. 2017. These applications are hereby incorporated by reference herein.

FIELD OF THE INVENTION

This invention relates to an ultrasound imaging system and method, in particular for determining stroke volume.

BACKGROUND OF THE INVENTION

Outflow of blood from the left or right ventricle of the heart is a parameter used by clinicians in a range of diagnostic and therapeutic applications. Total outflow of blood during a single cardiac cycle (a single heartbeat) is known as the (left-ventricular) stroke volume and outflow of blood per minute is known as cardiac output. Both are key parameters used in a range of clinical applications.

One important use of stroke volume is in assessing intravenous fluid responsiveness during hemodynamic fluid intervention.

When breathing, the lungs expand and contract. These volume changes lead to changes in intrathoracic pressure, the pressure being lower during inspiration than during expiration. The pressure changes have an impact upon the hemodynamic function of the heart; in particular the effective force exerted on the left ventricle by the intrathoracic pressure is lower during inspiration than during expiration, resulting in reductions in diastolic volumes.

This effect can be measured indirectly in changes in systolic blood pressure. Large blood pressure excursions (>10 mmHg, i.e. >around 1333.22 pascals), dubbed, pulsus paradoxus, are associated with conditions such as cardiac tamponade and asthma, and are used to manage optimal fluid therapy in patients with acute circulatory failure.

During respiratory support of hemodynamically unstable patients, mechanical ventilation is often used under anesthesia. Positive pressure is exerted in the lung from an external device, eliciting volume expansion and the inspiratory phase of ventilation. However, the absolute air pressures that the respiratory bronchioles and alveoli experience are different than those encountered during regular breathing, where movement of the diaphragm creates a volume that is filled by atmospheric air under the positive pressure gradient. As a result, the hemodynamic effect is reversed during mechanical ventilation, resulting in reversed pulsus paradoxus.

Lacking a real-time method to track systolic and diastolic volumes of the left or right ventricle, clinicians resort to tracking the change in blood pressure during the respiratory cycle in order to evaluate the potential effect of additional fluids on the function of the heart. While this indirect method is functional, the process of obtaining time trace recordings of blood pressure near the heart is limited to patients with invasive radial or intra-cardiac catheters in place. Furthermore, blood pressure recordings are an indirect method of surveying preload and afterload pressures on the left ventricle and atrium.

Currently, methods to predict the response to intravenous fluids during hemodynamic management rely on real-time blood pressure trace analysis. Reuter et al. in "Optimizing fluid therapy in mechanically ventilated patients after cardiac surgery by on-line monitoring of left ventricular stroke volume variations. Comparison with aortic systolic pressure variations," *Br. J. Anaesth.*, vol. 88, no. 1, pp. 124-126, January 2002 describe a method using continuous arterial pulse contour analysis (using a pulsed contour cardiac output (PiCCO) monitor) to estimate stroke volume in real-time. This approach performs relatively well compared to the standard systolic pressure variation methodology (+/−8%), but still requires an invasive femoral catheter. Furthermore, pulse contour analysis has its own limitations with regard to estimating stroke volume, such as variability of the pressure transducer location relative to the phlebostatic axis.

Cardiac output is also a key clinical parameter used for informing treatment of hemodynamic conditions and is related to stroke volume via heart rate, namely: Cardiac Output=Stroke Volume×Heart Rate.

One approach to measuring stroke volume (or cardiac output) directly is the use of ultrasound imaging methods.

For instance, it is known that two-dimensional Doppler (transesophageal (TEE)) ultrasound of the left-ventricular outflow tract (LVOT) can provide an estimated stroke volume continuously by monitoring flow through the tract during the cardiac cycle.

This method requires a trained sonographer or cardiologist to conduct two exams of the left ventricular outflow tract to measure CO. First, typically m-mode, ultrasound imaging is performed to measure the diameter of the LVOT, from which an average cross-sectional area can be estimated from a circular assumption. Next, spectral Doppler imaging is performed to estimate the maximum blood velocity over a cardiac cycle. Together, these parameters provide a relatively accurate estimate of CO, but require a trained user and are difficult to repeat.

In addition, it is subject to considerable variability due to the requirement to maintain the probe positioning unchanged over multiple cardiac cycles and the need to perform an estimation of LVOT diameter. It is not possible for this method to be performed without a trained sonographer or cardiologist.

In addition, this approach requires continuous collection of data throughout the duration of the cardiac cycle.

An improved ultrasound-based approach to determining stroke volume is sought which can remedy one or more of the above identified deficiencies.

SUMMARY OF THE INVENTION

The invention is defined by the claims.

According to an aspect of the invention, there is provided an ultrasound imaging system for determining stroke volume of a heart, comprising: an input for receiving acquired ultrasound data of a heart by an ultrasound transducer unit; and a controller adapted to:

perform an initial assessment procedure in which initial ultrasound data is acquired using the transducer unit, and a Doppler processing technique is applied to the initial ultrasound data to determine presence or absence of a regurgitant blood flow from a ventricle to an atrium of a heart captured in the initial ultrasound data;

responsive to determining absence of regurgitant flow, implement a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of said ventricle of the heart at each of said time points, and stroke volume is determined by calculating a change in said volume between said time points;

responsive to determining presence of a regurgitant flow, implement a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles; and generate output information based on the determined stroke volume.

The invention is based on the realization of the inventors that 3D ultrasound image data could be used to observe the dimensions of the volumetric boundary of the left ventricle (LV) or right ventricle (RV) directly at each of the end systolic and end-diastolic phases. By calculating the difference between these volumes, an estimate of stroke volume can be determined. Either the left ventricle or right ventricle can be used to estimate stroke volume.

Segmentation techniques provide a highly accurate means of identifying and measuring the LV or RV volume at each of the two phases. In addition, since volumes are observed directly, data need only be collected at two time points: once at end systole and once at end diastole, in contrast to Doppler flow based methods which require continuous data collection. This saves resources, time, and can increase frame rate.

However, the inventors have also realised that this method though simple and reducing data collection may not be accurate when regurgitant flow exists (backward blood flow from the left or right ventricle into the left or right atrium during systole). In these cases, simple volumetric change of the LV or RV may not yield an accurate estimate of true stroke volume.

Hence, the present invention proposes performing an initial assessment procedure in which it is determined whether regurgitant flow exists. This is performed using Doppler techniques applied to an initial ultrasound data. If regurgitant flow does not exist, stroke volume is determined using segmentation of 3D ultrasound image data at each of end systole and end-diastole as discussed, the difference between them giving a measure of stroke volume. However, if regurgitant flow does exist, stroke volume is instead determined using an alternative method in which Doppler techniques are applied to ultrasound data continuously collected throughout a cardiac cycle.

In this way, a uniquely optimized approach to stroke volume determination is provided wherein, absent regurgitant flow, a direct, 3D ultrasound segmentation based method is applied requiring only minimal data collection, and in the presence of regurgitant flow a back-up Doppler method is applied to ensure accuracy in all circumstances.

By regurgitant flow is meant 'backwards' flow into the left or right atrium from the left or right ventricle, in particular during systole when blood is predominantly being evacuated from the left ventricle. Regurgitant ventricular flow means that a simple difference in ventricular volumes may not be accurate as some blood assumed to have exited due the volume change may in fact have returned to the respective atrium, reducing the total volume outflow from the heart during that cardiac cycle Stroke volume can be estimated using volume changes or blood outflows from either the left or right ventricle (LV or RV). The method may in examples be performed in respect of only one of the LV or RV. In alternative examples, the method may be performed in respect of both the LV and RV. The difference in the estimated stroke volume determined for each of the LV and RV may be compared in some examples, since any disparity can be an indication of cardiac pathology.

In some examples, an assessment may be made of both the LV and RV to determine presence or absence of regurgitant flow. A stroke volume may be determined in respect of one or both based on the results. Different of the first and second imaging procedures may be used for each depending upon presence or absence of the regurgitant flow.

Presence or absence of regurgitant flow may be determined through Doppler analysis applied to ultrasound data acquired of the mitral valve region (in the case of the left ventricle) and/or the tricuspid region (in the case of the right ventricle). The mitral and tricuspid valves mediate blood flow between the left atrium and left ventricle and right atrium and right ventricle respectively.

In accordance with one or more embodiments, a location of the mitral valve and/or the tricuspid valve may be first identified by acquiring a preliminary ultrasound data set (e.g. by using B-mode imaging), and segmenting the data set to identify a location of the respective valve.

By end-systolic and end-diastolic time points is meant temporal points at the end of systole (contraction) of the heart and at the end of diastole (filling/expansion) of the heart.

In one of the embodiments the ultrasound imaging system for determining stroke volume of a heart may further comprise the ultrasound transducer unit, which is controlled to acquire ultrasound data of the heart.

The initial ultrasound data may be acquired throughout all or just part of the cardiac cycle of the heart. The initial ultrasound data may for instance be acquired during just the systole phase of the cardiac cycle, as blood is exiting the left or right ventricle.

By 'determine a volume' may be meant determine an outer volume, i.e. determine a volume defined by an identified outer boundary of the left or right ventricle. Hence determining the volume of the ventricle at each of the end systole and end diastole phases may mean identifying an outer boundary of the ventricle and estimating a volume defined by the identified outer boundary.

By total blood flow may be meant the total quantity of blood which flows out of the ventricle during each cardiac cycle. By total blood flow may be meant net blood flow. Typically blood flows out of the left or right ventricle only during the systole phase. Hence the total blood flow out of the ventricle may be total blood flow out of the ventricle during the systole phase.

The identified total blood flow out of the heart during a given cycle may be equated to with stroke volume.

In examples, the output information may be indicative of either cardiac output or stroke volume, the former being determinable through simple multiplication by a heart rate for the subject. The heart rate could be obtained for instance using an ECG input to the controller, derived from ECG data being collected from the subject.

The further Doppler processing technique may comprise determining a total blood flow out of the ventricle of the heart through a ventricle outflow tract of the heart. Where the ventricle is the left ventricle, the outflow tract is the left ventricle outflow tract (LVOT). Where the ventricle is the right ventricle, the outflow tract is the right ventricle outflow tract (RVOT). The left ventricle outflow tract is the main outflow blood vessel of the left ventricle. The right ventricle outflow tract is the main outflow blood vessel of the right ventricle.

The further Doppler processing technique may include determining an indication of blood velocity out of the ventricle throughout the cycle, and subsequently determining a total blood flow out of the ventricle based upon the velocity indication and geometric dimensions of the respective ventricular outflow tract. The geometric dimensions may be determined by the system (described in greater detail below) or may be stored or manually input by a user for instance.

In an advantageous set of embodiments, the second imaging procedure is optimized in accordance with a unique approach to reduce or eliminate the need for expert clinical involvement in the data collection method.

In particular, in accordance with one or more embodiments, the second imaging procedure may comprise identifying a region within a field of view of the ultrasound transducer unit occupied by a ventricle outflow tract (LVOT or RVOT) of the heart and controlling the transducer unit to acquire ultrasound data representative of or corresponding to only said region.

Once the location of the ventricle outflow tract within the field of view is known, the controller may direct the transducer unit (for instance comprising an array transducer) to steer or direct ultrasound beams onto the ventricle outflow tract, so that this anatomical region is effectively isolated for examination. This eliminates the need for a clinician or trained operator to physically control the positioning of the transducer unit so as to maintain ultrasound beams directed on the ventricle outflow tract.

The transducer unit need only be manually positioned once, in a position such that the LVOT or RVOT (and the LV or RV more broadly) are within its broad field of view (i.e. the field within which ultrasound beams are able to be steered by the transducer unit). This approach enables continuous, autonomous stroke volume or cardiac output monitoring in settings such as intensive care units or in an operating room for example.

In advantageous examples, the identifying a region comprises capturing a first 3D ultrasound image data set representative of the whole field of view of the transducer unit and applying an image segmentation technique to the data set to identify the region occupied by the ventricle outflow tract.

This approach advantageously combines 3D ultrasound segmentation methods with those of Doppler ultrasound to allow for accurate measurement of ventricular outflows at high sampling frequency without the need for a clinician to continuously maintain the position of the ultrasound transducer unit. In addition, by using the segmentation approach of the present embodiment, positioning of the transducer can, according to examples, be repeatedly checked in a fast and straightforward manner by recurrently repeating the calibration process of capturing and segmenting 3D image data and identifying the ventricle outflow tract. Alternatively motion detection of the transducer unit can be performed by filtering the Doppler ultrasound data to identify tissue motion portions. Any shifts in the position of the ultrasound transducer unit are hence quickly corrected by re-performing the 3D image data collection and segmentation to identify the ventricle outflow tract position.

In advantageous examples, the segmentation technique may be a model-based segmentation (MBS) technique. MBS typically adapts a full model of the heart to acquired, e.g. B-mode, ultrasound image data. This enables locations of anatomical structures, such as the left ventricular outflow tract (LVOT) or right ventricular outflow tract (RVOT), to be resolved, guided for instance by the location of adjacent, resolvable structures, and the general cardiac anatomy.

The second imaging procedure may further comprise identifying a size of the ventricle outflow tract. This may be done based on the segmentation of the captured 3D image data. Segmentation can be used to estimate sizes of anatomical bodies. Preferably the size is a cross-sectional area of the ventricular outflow tract or may be a diameter or width of the ventricular outflow tract. The size may be used in combination with a directly measured flow velocity spectrum during each single cardiac cycle to calculate an estimate for stroke volume.

In particular, the step of determining the total blood flow out of the ventricle may comprise determining a velocity of blood flow through the ventricle outflow tract, and estimating a total blood flow based on said velocity and on the determined size of the outflow tract.

An average flow velocity may in certain examples be calculated and multiplied by the cross-sectional area to derive total blood flow. Alternatively, in further examples, an integral $\int v(t) \cdot A \, dt$ over the cardiac cycle may be calculated, where v(t) is measured blood flow velocity as a function of time and A is cross sectional area of the ventricle outflow tract. This thus yields total volume outflow during a single cycle, i.e. stroke volume.

In accordance with one set of embodiments, a stroke volume may be estimated or determined in respect of both a left ventricle and a right ventricle.

Accordingly, in accordance with one or more embodiments, the controller may be adapted to perform the initial assessment procedure in respect of both a left ventricle and right ventricle of the heart, and responsive to determining absence of regurgitant flow from the left ventricle and/or right ventricle, perform the first imaging procedure in respect of the left ventricle and/or right ventricle; and responsive to determining presence of regurgitant flow from the left ventricle or right ventricle, perform the second imaging procedure in respect of the left ventricle and/or right ventricle.

To this end, the whole procedure, including the initial assessment procedure and first or second imaging procedure may be performed in respect of both the left ventricle and right ventricle.

The stroke volume estimation derived for the left and right ventricles may be compared in examples, since disparity between the two may be an indication of a cardiac pathology.

In alternative examples, the controller may be adapted to perform the initial assessment procedure in respect of only one of a left ventricle or a right ventricle. Here, stroke volume is determined for only the left ventricle or only the right ventricle.

The initial assessment procedure hence may comprise determining presence or absence of regurgitant flow from a left ventricle to a left atrium or from a right ventricle to a right atrium, As noted above, variation in stroke volume is a key parameter in assessing hemodynamic response to intravenous fluid intervention.

Accordingly, in accordance with one or more embodiments, the first and/or second imaging procedure may comprise acquiring ultrasound image data corresponding to multiple heart cycles, determining a stroke volume for each heart cycle, and further determining an indication of a variation in stroke volume between heart cycles.

The indication of a variation in stroke volume may in examples be a data set listing determined stroke volumes at each of a plurality of different cardiac cycles. The indication of a variation may in examples be an indication of a trend in stroke volume over time, e.g. a gradient of stroke volume as a function of time. The indication of variation may be an indication of an absolute or relative change in the stroke volume between the last two measured cardiac cycles. Any other indication of variation may also be used.

An indication of a change in cardiac output may additionally or alternatively be determined.

In accordance with the first imaging procedure, the controller may be in examples be adapted to communicate the generated output information and/or the determined indication of variation in stroke volume to an intravenous fluid administration device being in communicative relationship with the controller.

The fluid administration device may be external to the ultrasound imaging system of the invention or may in examples be a part of the imaging system. The fluid administration system may be adapted to adjust a fluid administration regime based on the stroke volume or cardiac output values represented in the output information, or based upon the indication of variation in one or both of these values.

The ultrasound transducer unit may in preferred examples comprise a transducer array operable to generate ultrasound beams, the beams having a controllable directionality. The beams in this case are preferably steerable. Control of an ultrasound transducer array to form focused beams being steerable between different directions is well known in the art. The controller may include microbeamformer functionality to control or direct beamforming and beam steering. Alternatively, a separate microbeamformer unit may be provided which performs this function.

This may permit for instance localized directing of ultrasound beams onto just the ventricular outflow tract (left or right) in accordance with the second imaging procedure. It may be permit straightforward switching between the two imaging procedures, and between different required fields of ultrasound examination.

In examples, the controller may be adapted to receive an electrocardiogram (ECG) signal input representative of the cardiac cycle, and use the signal input for synchronizing ultrasound data acquisition with the cardiac cycle. This is known as ECG gating. The ECG signal input may be derived from sensors applied to the subject under examination.

The ECG signal permits temporal tracking of the phases of the heart cycle, so that data collection can be timed to coincide with the beginning and end of each heart cycle for instance. For the first imaging procedure, the ECG input signal permits for instance identification of the end-systolic and end-diastolic phases, so that ultrasound data collection can be timed to coincide with these time points only. For the second imaging procedure, the start and end of each cardiac cycle can be identified, so that data collection can be timed to extend continuously throughout each given cycle.

ECG gating may be unnecessary where the volumetric frame rate of ultrasound data is high (e.g. 25 Hz). In this case, it can be assumed with reasonable confidence that the smallest measured volume of the ventricle throughout the cycle is indeed the smallest volume that the ventricle reaches during that cycle. In particular, if the volume of the left or right ventricle is measured with a volumetric rate that is greater than (or equal to) twice its frequency content, then the smallest and largest volume points can be reconstructed with a good degree of confidence using just ultrasound data.

ECG gating is particularly useful however where volumetric frame rate is low, and so where the end systole and end diastole time points cannot be determined without extra tools.

The determined output information related to the stroke volume may be processed or used by the system in different ways. The output information may be stored in a local memory or may be communicated for storage in a remote memory or data store. In examples, the output information may be communicated to a display device to be displayed to a user.

In accordance with one or more embodiments, the system may further comprise a display unit, the controller being adapted to control the display unit to display a visual representation of the output information.

The output information may be communicated to a further system or device for use in monitoring or directing care or treatment of the subject. In examples, the controller may be communicatively coupled with a patient monitoring device and adapted to communicate the output information to the patient monitoring device.

The communicative coupling may be wired or wireless in examples.

As noted above, in accordance with any embodiment, the output information may be indicative of a cardiac output, the cardiac output being determined based on the determined stroke volume and based upon a heart rate for the heart. The heart rate may be obtained for instance from a signal input to the system provided from any suitable heart or pulse rate sensor or related sensor (e.g. a PPG sensor). The heart rate may be obtained from a signal input from an ECG sensor for instance.

The output information may be in the form of a data output.

In accordance with one or more embodiments, the ultrasound transducer unit may for instance be a transesophageal echocardiography (TEE) probe or a transthoracic echocardiography (TTE) probe. Either such probe permits placement within or on the body of the subject so as to provide a transducer field of view permitting examination of the heart. In one or more examples, the controller may be comprised by the ultrasound transducer unit. For instance the controller may be incorporated into the transducer unit or integral with the transducer unit.

In examples, the transducer unit may be a smart probe comprising a transducer array for acquiring ultrasound data and including an integrated controller.

In accordance with alternative examples, the controller may be separate to the transducer unit. For instance, the ultrasound imaging system may be a cart-based system (i.e. a mobile system), wherein a base unit of the cart comprises the controller and the transducer unit (e.g. a probe) is communicatively connected to the controller.

Examples in accordance with a further aspect of the invention provide a patient monitoring system, comprising:
  a patient monitoring device;
  an ultrasound transducer unit operatively coupled with the patient monitoring device, for acquiring ultrasound data of a heart; and
  a controller for controlling the ultrasound transducer unit and determining stroke volume of said heart, the controller adapted to
  perform an initial assessment procedure in which initial ultrasound data is acquired using the transducer unit, and a Doppler processing technique is applied to the initial ultrasound data to determine presence or absence of a regurgitant blood flow from a ventricle to an atrium of a heart captured in the initial ultrasound data;

responsive to determining absence of regurgitant flow, implement a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of said ventricle of the heart at each of said time points, and stroke volume is determined by calculating a change in said volume between said time points;

responsive to determining presence of a regurgitant flow, implement a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles.

The transducer unit may comprise the controller in examples. The transducer unit may be a smart probe comprising the controller.

In other examples, the patient monitoring device may comprise the controller.

The communicative coupling may be wired or wireless in examples.

Examples in accordance with a further aspect of the invention provide an ultrasound imaging method, the method making use of an ultrasound transducer unit for acquiring ultrasound data of a heart, the method comprising:

performing an initial assessment procedure in which initial ultrasound data is acquired using the transducer unit, and a Doppler processing technique applied to the initial ultrasound data to determine presence or absence of a regurgitant blood flow from a ventricle to an atrium of a heart captured in the initial ultrasound data;

responsive to determining absence of regurgitant flow, implementing a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of a ventricle of the heart at each of said time points, and stroke volume is determined by calculating a change in said volume between said time points;

responsive to determining presence of a regurgitant flow, implementing a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles; and generating output information based on the determined stroke volume.

According to certain embodiments, the ultrasound imaging method may be performed as an ex vivo imaging method (i.e. non-invasively), for example based on use of an ultrasound transducer unit positioned external of the body. In this case the method may hence be an imaging method making use of an ultrasound transducer unit for ex-vivo acquisition of ultrasound data of a heart.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
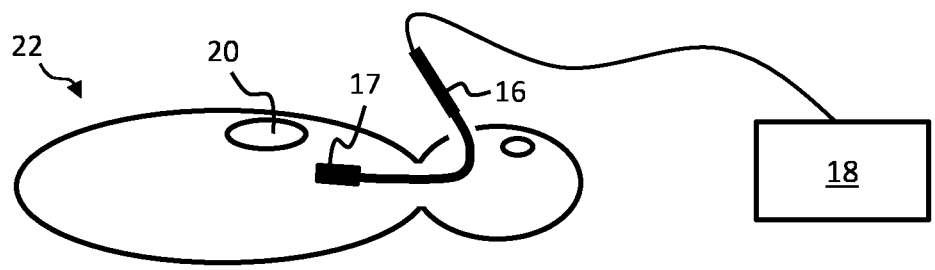
FIG. 1 schematically depicts general arrangement of components of a system in accordance with one or more embodiments.

The invention provides an ultrasound imaging system for determining stroke volume and/or cardiac output. The imaging system includes a transducer unit for acquiring ultrasound data of a heart of a subject, and a controller. Alternatively the imaging system may include an input for receiving the acquired ultrasound data by a transducer unit rather than the unit itself. The controller is adapted to implement a two-step procedure, the first step being an initial assessment step, and the second being an imaging step having two possible modes depending upon the outcome of the assessment. In the initial assessment procedure, it is determined whether regurgitant ventricular flow is present. This is performed using Doppler processing techniques applied to an initial ultrasound data set. If regurgitant flow does not exist, stroke volume is determined using segmentation of 3D ultrasound image data to identify and measure the volume of a ventricle at each of end systole and end-diastole, the difference between them giving a measure of stroke volume. If regurgitant flow does exist, stroke volume is determined using Doppler techniques applied to ultrasound data continuously collected throughout a cardiac cycle.

Determination of stroke volume is valuable in a range of clinical applications. Variation in stroke volume can be used to assess response to hemodynamic intravenous fluid intervention.

Cardiac output (equal to the product of stroke volume and heart rate) is also an important clinical parameter.

Ultrasound represents a favorable approach to measuring these parameters. Various non-ultrasound based approaches do exist, such as indirect measurement using blood pressure, but as discussed above, these suffer various deficiencies, including limited accuracy and reliability. It is difficult to obtain an absolute measure of stroke volume using blood pressure measurements, as opposed to a relative measure of a measure of change in stroke volume.

A range of presently available methods are outlined in summary in Table 1 below, and it can be seen that for each there are deficiencies.

TABLE 1

| Interaction Mode | Device | Modality | Measurement Frequency | Limitations |
| --- | --- | --- | --- | --- |
| Manual | TTE (transthoracic probe) or TEE (transoesophageal probe) | Ultrasound | Single | Requires trained user Non-continuous Poor repeatability Limited accuracy |
| Automatic | Pulsed contour cardiac output (PiCCO) monitor | (Blood Pressure) Pulse Contour Analysis | ~1 per second | Inaccurate Invasive |
| Automatic | Swan-Ganz Pulmonary Artery Catheter | Thermodilution | ~1 per 1-10 seconds | Invasive Imprecise Poor temporal resolution |
| Semi-automatic | USCOM | Echocardiography | ~1 per second | Requires trained user Inaccurate |
| Semi-automatic | NICOM | Bioimpedance | ~1 per second | Relative measurement Invasive Interference |

Ultrasound offers a means of obtaining a direct measure of stroke volume. However, currently implemented ultrasound approaches suffer deficiencies in terms of reliability, accuracy and reproducibility.

The most accurate approaches use Doppler ultrasound imaging to monitor and measure blood flow out of the left ventricular outflow tract (LVOT)—a large vessel which carries all blood exiting the left ventricle—during systole. Since blood flow varies with time, the temporal resolution offered by ultrasound imaging makes it an attractive approach. Cardiac output (and/or stroke volume) estimation techniques based on ultrasound imaging of this kind are widely used, in particular for immediate spot checks of cardiac output.

However, as discussed above, this approach requires a trained cardiologist or sonographer to continuously maintain the position of an ultrasound imaging probe focused toward the LVOT throughout multiple cardiac cycles. Should the probe shift or move inadvertently between cycles, accuracy of results is affected. It is difficult, even for experts in the procedure, to maintain absolute stasis of the probe. The requirement for hands-on medical control also makes this method inappropriate for ongoing or continuous monitoring, e.g. in intensive care units or in the operating room.

The Doppler approach also requires continuous data collection throughout at least the systole phase of each cardiac cycle (so blood flow can be continuously monitored and measured).

The present invention proposes a simple 3D segmentation based approach, wherein 3D ultrasound data is collected only once at the end of each of systole and diastole of the heart, the data being segmented to identify and quantify a volumetric boundary of the left or right ventricle at each point, and a stroke volume determined as the difference between them.

In particular, over a cardiac cycle, the shape of the left or right ventricle is determined from volumetric image data of cardiac tissue. Volumes are calculated from the end-diastolic and end-systolic frames, yielding stroke volume on a beat-by-beat basis. This method produces a minimally invasive, direct assessment of ventricular volumes that the clinician can use to predict and guide fluid management.

This approach improves reliability and reproducibility. As the method applies segmentation to each collected image data set, shifts in the position of the transducer unit have little effect upon the accuracy of the measurement as the segmentation identifies the position (and size) of the ventricle anew within each data set.

The method can be applied to either the left ventricle or the right ventricle or both to determine a stroke volume. It can be performed in respect of both the left ventricle and right ventricle and a separate stroke volume estimation obtained for each. Comparison of the two can provide indication of certain cardiac pathologies.

The approach is only fully accurate however where there is no regurgitant blood flow into the ventricle (left or right respectively) during diastole. Absent this condition, simple volumetric change of the ventricle may not accurately reflect the true stroke volume. Thus, to ensure accuracy in all cases, the system of the present invention is configured to check for regurgitant flow and implement the volume-change based approach where there is no regurgitation, and implement a continuous Doppler flow based approach where there is regurgitation.

Furthermore, in preferred examples, in the latter case, an improved Doppler flow based approach is applied which advantageously incorporates image segmentation techniques to provide automated focusing of ultrasound beams on the ventricular outflow tract, thereby allowing implementation of the system in the absence of any specialist medical operators. These preferred examples hence improve upon the accuracy and reliability of known Doppler ultrasound methods for measuring stroke volume and cardiac output.

FIG. 1 schematically depicts the basic hardware configuration in accordance with one example of the system of the invention. The system comprises an ultrasound transducer unit 16, in this case in the form of a transesophageal echocardiography (TEE) probe. The probe comprises at an imaging end an ultrasound transducer array 17 operable to generate ultrasound beams having beams having controllable directionality.

In use, the probe is positioned by a clinician in a suitable positon such that a heart 20 of a subject 22 is within a broad field of view of the transducer array 17 of the transducer unit

16. In this case, as the transducer unit is a TEE probe, the TEE probe is located in a suitable position within the esophagus of the subject 22.

The probe is operatively coupled to a controller 18 which controls acquisition of ultrasound image data using the transducer unit 16 for determining a stroke volume and/or cardiac output of the heart 20.

By way of illustration, steps implemented by the controller will now be described with reference to an example in which just the left ventricle is assessed and measured. However, it is to be understood that the same procedural steps may be applied alternatively or additionally to the right ventricle, and all references to the left ventricle should be understood as applicable also to determining stroke volume using the right ventricle.

The controller 18 is adapted to first carry out an initial assessment procedure in which initial ultrasound data is acquired of the heart 20 at least during a systole phase of the cardiac cycle. It is then determined whether there is regurgitant flow present.

Figure 2:
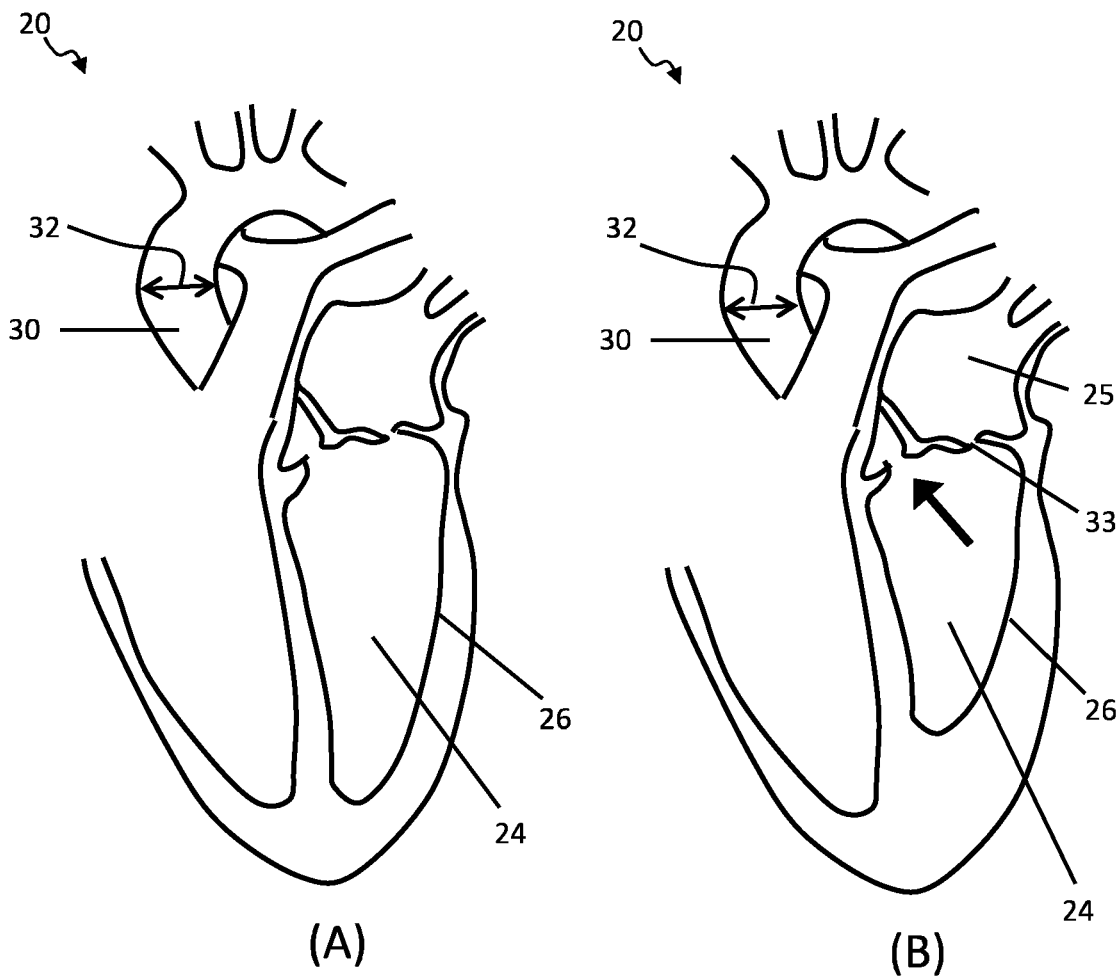
FIG. 2 illustrates contraction during systole phase of a left ventricle.

This is illustrated with reference to FIG. 2 which schematically depicts a heart at the start (A) and end (B) of the systole phase (or equivalently, at end-diastole (A), and end systole (B)). As shown, during systole, the volume of the left ventricle 24 contracts, forcing blood to exit the ventricle via the left ventricle outflow tract (LVOT) indicated generally at 30, with a diameter of the tract indicated by 32.

Figure 3:
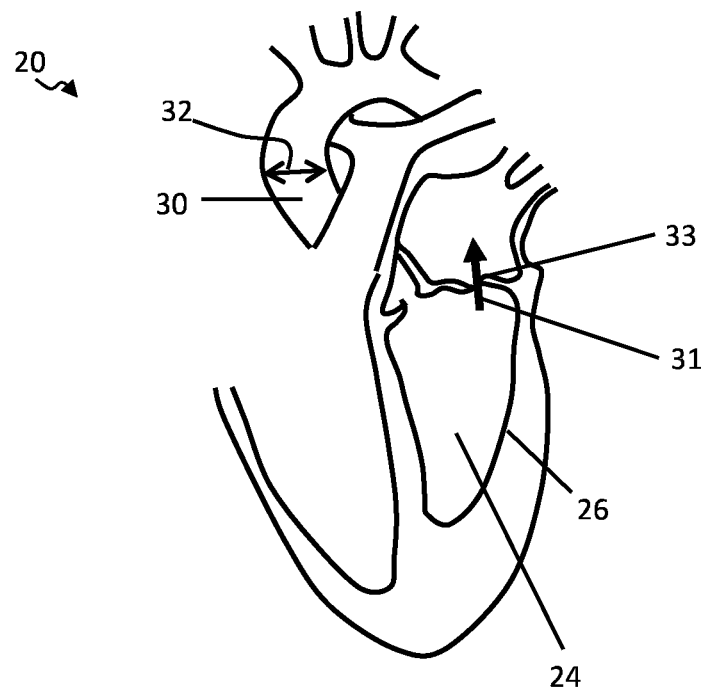
FIG. 3 illustrates regurgitant flow.

In the case of regurgitant flow, blood flows backwards from the ventricle 24 to the left atrium 25 via the mitral valve 33, as shown by arrow 31 in FIG. 3. This backwards flow can be detected by capturing ultrasound data of the heart (or at least the mitral valve 33 region) during the systole phase and applying Doppler analysis to detect the reverse directional flow.

Where stroke volume is to be determined for the right ventricle instead of the left, regurgitant flow manifests in backward flow from the right ventricle to the right atrium via the tricuspid valve. This backwards flow can be detected by capturing ultrasound data of the heart (or at least the tricuspid valve region) during the systole phase and applying Doppler analysis to detect the reverse directional flow.

By way of example only, the following explanation is described with reference to the procedure for the left ventricle only.

Advantageously, the initial assessment procedure makes use of the improved Doppler imaging technique discussed above, wherein image segmentation is used to identify a region of the field of view of the transducer unit which is occupied by the mitral valve 33.

In accordance with this approach, the ultrasound transducer probe 16 is initially positioned by a clinician within a subject's esophagus in a position such that the subject's heart 20, or at least the mitral valve region 33 are within a broad field of view of the transducer probe e.g. positioned within angular range of steerable beams of a transducer array 17 of the probe.

An initial 3D ultrasound image data set is then acquired of the broad field of view.

The greyscale data thereby acquired is subsequently processed by the controller 18 to apply image segmentation.

Image segmentation is a well-known procedure in the field of image processing whereby a (digital) image is partitioned or divided into a plurality of sectors or regions according for instance to common properties possessed by pixels falling within those regions. For instance, image segmentation may typically be applied to identify or locate objects within a broader image and to identify boundaries within images (e.g. lines, curves, contours).

In the present application, image segmentation allows an ultrasound image to be processed to identify or locate anatomical bodies or regions within the image and locate boundaries of said bodies or regions.

The image segmentation may preferably be model-based image segmentation. Model based segmentation makes use of common structural or geometrical patterns characteristic of a particular anatomical region or body to more accurately identify anatomical bodies within captured images. In particular, a probabilistic model is employed concerning likely shapes or contours for certain anatomical features. The parameters encoded within this model may then be applied as constraints when segmenting image data to more accurately and precisely identify boundaries of particular geometrical features or regions which are of interest.

For instance in the present application, model-based segmentations may make use of a model associated with the cardiac region, or may more particularly make use of a model of the left or right ventricular region, including the mitral valve, tricuspid valve and left or right ventricular outflow tract.

Suitable model-based segmentation algorithms for this purpose are known in the art. See for example Ecabert et al., "Automatic Model-Based Segmentation of the Heart in CT Images". IEEE TRANSACTIONS ON MEDICAL IMAGING, 27(9), 2008 which describes model-based segmentation approaches which could be applied to ultrasound data acquisitions of the present invention.

Segmentation for the present case is applied such as to produce location information corresponding to the mitral valve 33, in particular the region of the broad field of view occupied by the mitral valve. For instance co-ordinates of an outline of the mitral valve may be determined or any other representation of the location.

The determined location information is then fed to a Doppler beamforming unit (which may be a separate unit comprised by the controller 18 for instance, or may be functionally integral to the controller, meaning that the controller carries out the function of a Doppler beamforming unit).

A transducer array 17 of the transducer probe 16 is then controlled to focus and direct (i.e. steer) ultrasound beams onto the identified region of the mitral valve 33 to the exclusion of other regions. Ultrasound beams are transmitted throughout the duration of at least the systolic phase of the cardiac cycle. Ultrasound data is thus collected corresponding to the mitral valve region and returning echo signals (e.g. echo pulses in the case of pulsed ultrasound) are Doppler processed to derive a blood flow velocity function for blood flowing through the mitral valve as a function of time. This function may be processed to determine occurrence of negative velocities, or velocities in a direction towards the left atrium 25 (i.e. regurgitant flow).

Where regurgitant flow is not identified, the controller 18 is adapted to implement a first imaging procedure in which a transducer array 17 of the transducer probe 16 is controlled to acquire 3D ultrasound image data across a broad field of view encompassing the heart 20 or at least encompassing the left ventricular region 24 of the heart. In alternative examples, the broad field of view may encompass at least the right ventricular region.

In particular, for the first imaging procedure, the ultrasound transducer unit (the ultrasound probe 16 in the present example) is in advantageous examples capable of acquiring three-dimensional imaging data at frame rates at or above 10

Hz, and capable of streaming collected data to the controller 18. The probe may be physically retained in place, e.g. using mechanical retaining means. The probe is preferably held in place in a position such as to enable a sufficient field of view of the heart 20. For transesophageal use (such as in the example of FIG. 1), probe stability may be ensured by correct and stable positioning within the esophagus. For transthoracic use, a probe holder or patch may be used for instance.

The probe 16 is controlled to capture 3D ultrasound data at only end diastole (FIG. 1; A) and end systole (FIG. 1; B) points in the cardiac cycle of the subject 22. The controller 18 is preferably communicatively coupled with an ECG unit (not shown) having ECG sensors coupled to the subject. A signal input received at the controller from the ECG unit is used to identify timings of end diastole and end systole such that data collection can be controlled to coincide with these phases. This efficiently minimizes data collection.

Each collected ultrasound image data frame is processed by the controller 18 in accordance with an image segmentation algorithm. Image segmentation is well known procedure in the art, and as discussed above, suitable algorithms exist for implementing segmentation in examples of the present invention.

The image segmentation derives from the (greyscale) ultrasound 3D data a shape profile of a volumetric outer boundary 26 of the left ventricle 24 at each image frame (e.g. at end diastole (A) and end systole (B)). The segmentation algorithm may in examples make use of any suitable image processing tools known in the art, including e.g. machine learning tools. The algorithm may make use of model-based image segmentation, as discussed above.

The derived left-ventricle boundary 26 shape information is then processed by the controller 18 and a volume or estimated volume of the left ventricle 24 at each of end diastole and end systole is calculated. The calculated volume at end systole is subtracted from that at end diastole to derive a change in volume. The change in volume may be equated with stroke volume, i.e. the total outflow of blood from the left ventricle 24 during a heart cycle.

The process may be repeated for multiple cardiac cycles to derive stroke volume values for a plurality of cardiac cycles.

In accordance with a further optional step, the controller 18 may further process derived stroke volume values for multiple cardiac cycles to derive stroke volume variation information.

This information may usefully be combined with other patient specific information such as ECG readings for the subject 22, intravenous fluid volume dosing information and clinical guidelines before being communicated to a user. This may improve efficiency of use of the device by conveniently providing associated clinical information together.

In accordance with examples, the system may comprise a display unit (not shown) for displaying the derived stroke volume and/or stroke volume variation information to a user. The information may be displayed in a range of different formats. There may for instance be displayed real-time traces of stroke volume, stroke volume variation, intravenous fluid dosing history and stroke volume variation response to fluid dosing.

Figure 4:
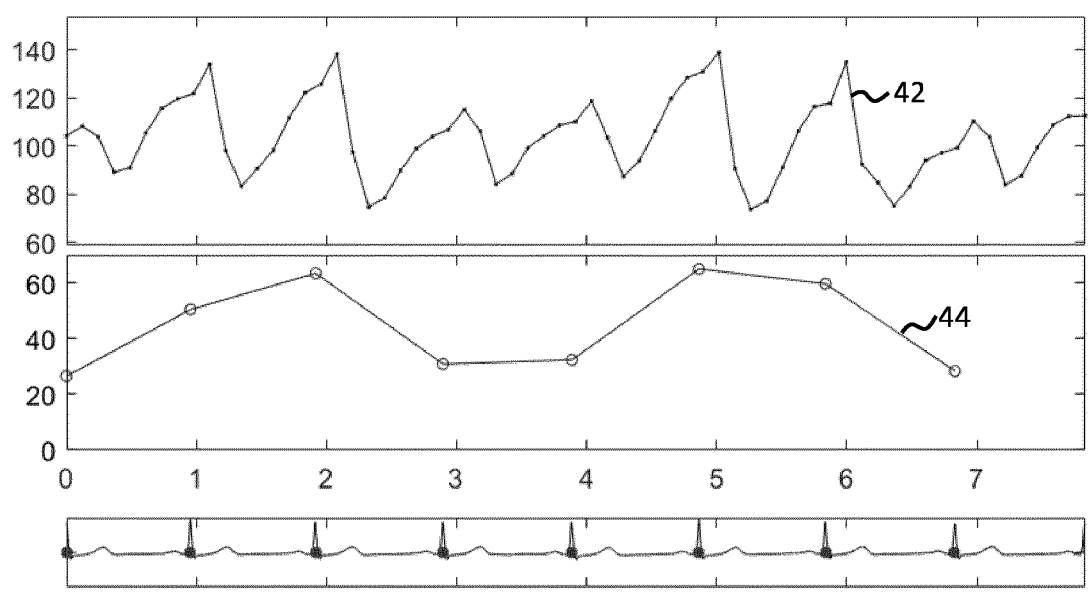
FIG. 4 illustrates a real-time stroke volume trace as generated in accordance with an embodiment.

FIG. 4 illustrates an example real-time trace which may be displayed to a user by means of an associated display unit. Line 42 shows variation of ventricle volume (y axis; mL) over time (x axis; seconds) and line 44 shows variation in stroke volume (y axis; mL) over time (x axis; seconds).

The data shown was collected from a patient under mechanical ventilation. However, the system can be used for patients not under mechanical ventilation, even where a TEE probe is used, if the patient is able capable of taking deep breaths.

In accordance with examples, the derived stroke volume variation information may directly inform control or adjustment of intravenous fluid administration being applied to a patient, for instance adjusting dosage or timings. This may be based on a pre-stored mathematical relationship between stroke volume variation and intravenous fluid dosage response, or based upon a relationship between absolute stroke volume and ideal intravenous fluid dosage for instance.

Above has been described the first imaging procedure which the controller 18 implements in the case that the initial assessment procedure (described above) indicates no presence of regurgitant flow into the left ventricle 24 (at least during systole phase).

In the case that regurgitant flow is identified in the initial assessment procedure, the controller is adapted to instead carry out a second imaging procedure in which a Doppler based stroke volume determination method is carried out. This Doppler based method in the preferred embodiment to be described below advantageously employs ultrasound imaging methods to automatically acquire location information for the left ventricle outflow tract, enabling local focusing of beams on this area, avoiding the need for a trained user to continuously guide positioning of the probe. In alternative examples, the right ventricle and right ventricular outflow tract may alternatively or additionally be considered. For brevity of explanation, the procedure will be explained by way of example only with reference to the left ventricle.

Figure 5:
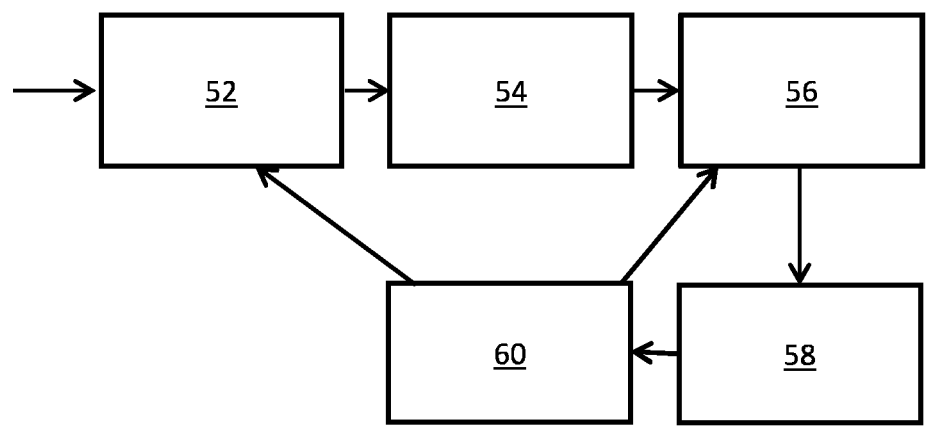
FIG. 5 shows a block diagram illustrating steps performed by the system in accordance with a second imaging procedure.

Steps of the second imaging procedure are schematically represented in block diagram form in FIG. 5.

As for the first imaging procedure, the ultrasound array 17 of the probe 16 is assumed to be pre-positioned by an operator such that the left ventricle outflow tract lies in a broad field of view of the transducer probe, i.e. within steering range of steerable beams of the transducer array. Example advantageous positioning may for instance provide a broad field of view aligned with the mid-esophageal (ME) aortic long axis, transgastric (TG) short axis, or transgastric (TG) long axis.

Upon initiation of the second imaging procedure (responsive to the initial assessment), the controller 18, in step 52, controls the ultrasound transducer unit (probe) 16 to acquire three dimensional (volumetric) ultrasound image data, the probe being pre-positioned for capturing images of the heart 20 of the subject 22. B-mode volumetric ultrasound imaging may for instance be employed to capture the 3D ultrasound image data.

Once volumetric image data has been acquired, in step 54, the (greyscale) data is segmented in accordance with an image segmentation algorithm (see above for a more detailed discussion of suitable image segmentation algorithms and means). The image segmentation is preferably model based image segmentation. The segmentation allows locations of anatomical structures or features within the imaged heart region to be identified, including the left ventricle outflow tract. The segmentation also allows size information pertaining to anatomical features to be identified. In particular, a cross-sectional area of the left ventricle outflow tract (LVOT) 32 is determined. The cross section area is determined or derived for at least one particular location, as indicated by arrow 32 in FIGS. 2 and 3, but may be determined for more than one location on the LVOT.

Note, where the procedure is performed for the right ventricle, the position and size of the right ventricle outflow tract (RVOT) is instead derived using image segmentation.

Derived co-ordinates of the LVOT may for instance be determined by means of the (e.g. model-based) segmentation of the ultrasound data. These are, in step 56, fed to a Doppler beamforming unit of the system which, based on the co-ordinates, controls the transducer array 17 of the probe 16 to steer or focus ultrasound beams locally onto the LVOT.

The Doppler beamforming unit may be comprised by the controller 18 or may be functionally integral to the controller, i.e. the controller performs the function of the ultrasound beamforming unit. Alternatively, the beamforming unit may be separate to the controller 18, for instance part of a broader diagnostic imaging system or patient monitoring system.

The transducer array is controlled to direct ultrasound beams spanning across the LVOT based on the derived LVOT cross-sectional area, and upon the known beam geometry. The Doppler gate location and length is to this end set based on a spatial range of image coordinates over the cardiac cycle. Ultrasound data is thereby collected corresponding to the LVOT and from which velocity information corresponding to blood flowing through the LVOT can be determined.

For the avoidance of doubt, 'Doppler gate location' is a term of the art meaning a region of interest for which ultrasound data is to be collected and for which Doppler flow measurements are to be acquired. The Doppler gate length refers to the size of this region of interest.

In the present case, the Doppler gate location and length is set to correspond with the location and size of the LVOT.

In the present preferred embodiment, determining and setting the gate location and length is performed automatically. As discussed above, image segmentation enables determination of the location within the image volume that the LVOT exists. The location of the LVOT can be examined over multiple frames in a cardiac cycle, by which can be determined a full range of locations that the LVOT has existed throughout that cardiac cycle ("spatial range of coordinates").

For example, the LVOT may in some cases exhibit oscillatory motion in space throughout the cycle. In this case, the full range of locations is larger than the true size of the LVOT. By contrast, if the LVOT is stationary (calm heart motion), the range of locations would extend no further than the static size of the LVOT throughout the cycle.

Once the location and size of the LVOT is known, the transducer array is controlled to focus or steer ultrasound beams onto this region such as to extend across the determined LVOT region for the duration of the cardiac cycle.

Ultrasound 'lines' are emitted from the transducer unit in sufficient quantity to cover the entire lateral and/or elevational extent of the LVOT region. Furthermore, to cover the axial dimension, the data may be processed with a time delay corresponding to the range of depths of the LVOT.

In an alternative example, rather than directing a bundle of beams across the full area of the LVOT, the transducer array 17 may be controlled to 'fire' beams sequentially across a region described by the LVOT. The target locations for the beam may be determined based on the LVOT geometry derived from the segmentation and the number of beams required may be derived based on known ultrasound beam width at the known depth of the LVOT. These values may typically be standard known parameters for a given ultrasound transducer.

In accordance with either approach, ultrasound data may be collected over a whole cardiac cycle, or at least over a systole phase of the cardiac cycle. Data may be collected continuously over the cardiac cycle or over the systole phase.

Upon acquisition of the ultrasound data corresponding to the LVOT, the controller 18, or a Doppler processing unit may process the derived data using a Doppler processing technique. Such techniques are commonly known in the art, and allow a spectrum of velocities to be derived for a given imaged region over a period of time. In the present case a spectrum of velocities can be derived for blood flowing through the left ventricle outflow tract (LVOT) over the cardiac cycle or over at least the systole phase of it (when blood is flowing out of the left ventricle).

The processing technique permits the controller 18 (or a separate Doppler processor) to derive a function of blood velocity through the LVOT over time (v(t)).

In certain examples, a low frequency filtering procedure can be applied to the derived Doppler ultrasound data to eliminate contributions caused by (small) inadvertent movement of the probe. The controller in this case may set an optimized cut-off frequency of filters, for enabling artifact-free quantification of higher frequency blood motion, while also allowing sufficient low frequency tissue motion content to pass to enable detection of probe motion.

In step 58, an effective Doppler angle is calculated based on cross-sectional area of the LVOT derived during the segmentation, and based on characteristics of the transmitted ultrasound beams (in particular the known steering direction of the generated beams). The angle between each of the transmitted beams and average flow vector directions at the LVOT target (as measured from the ultrasound data) are calculated. An average of these angles is then calculated to derive effective Doppler angle. The effective Doppler angle is then used to correct the spectral Doppler traces over the cardiac cycle, i.e. to derive an angle-corrected Doppler trace, from which an angle-corrected velocity-time function v(t) can be derived, Deriving Doppler angle based on image segmentation represents a significant improvement over previous methods where typically Doppler angle would be calculated manually by an operator (i.e. a cardiologist or a sonographer). When performed manually, errors can occur. Even small errors in Doppler angle calculation can directly lead to significant errors in resulting velocity measures, especially at angles over 60°.

A time integral may be taken over the product of the Doppler-angle-corrected velocity-time function v(t) and the cross-sectional area of the LVOT (derived in segmentation step 54 in order thereby to derive a total volume of blood flow through the LVOT over the cardiac cycle. Since the LVOT is the only outlet path from the left ventricle, this total blood flow provides a measure of stroke volume (SV). This can therefore be represented as follows $$SV = \int_{cycle} v(t) A dt$$

where A is the cross-sectional area of the left ventricle outflow tract and v(t) is the Doppler angle-corrected blood flow velocity-time function.

Finally in step 60, a motion detection procedure is performed. Here, the low-frequency portion of the acquired Doppler signal is isolated, for instance using a low-frequency filter. This portion represents the tissue-Doppler portion, i.e. the portion representing (relatively slower) motion of tissue as opposed to motion of blood. This signal can be processed to determine whether tissue motion exceeds a pre-determined threshold, i.e. if there has been movement of the probe exceeding a certain threshold.

In the case that there has not been any movement exceeding the threshold, the imaging procedure can loop directly back to Doppler ultrasound acquisition step 56 (i.e. without re-acquiring LVOT position information), and stroke volume re-determined for subsequent cardiac cycles, based on the new position information for the LVOT.

In the case that there has been movement exceeding the threshold, the procedure returns back to step 52 and widefield volumetric ultrasound data is once again acquired and segmentation 54 re-performed to re-acquire position co-ordinates for the LVOT. The procedure can then proceed to step 56 to acquire and process Doppler ultrasound and re-determine stroke volume for further cycles.

Hence, the second imaging procedure of FIG. 5 operates in a loop to acquire stroke volume (and/or, optionally, cardiac output, by multiplying stroke volume by subject heart rate) measurements for successive heart cycles. At the end of each cycle, probe movement detection 60 is carried out.

Although in the example outlined above, in steps 52 and 54, volumetric B-mode image data is acquired and segmented in order to acquire location information for the LVOT, in alternative examples, different means for acquiring location information may be used. This may be different imaging means. Different means may be preferred or necessary for example where volumetric (acquisition) frame rate is low (e.g. <~10 Hz). Low frame rate may arise as a result of applying high field-of-view or resolution settings for a particular patient, causing trade-offs in achievable frame rate.

Acquisition of size information for the LVOT can be performed using M-mode imaging of the LVOT, permitting determination of a cross-sectional area of the LVOT.

In traditional 2D ultrasound imaging, M-mode gathers continuous echo data along one "line" allowing the oscillation of a structure, such as a valve or tissue to be observed. From this information, the length of the structure can be determined. This approach can be extended to 3D imaging, allowing determination of the cross sectional area of a structure, i.e. in this case the LVOT.

In accordance with one or more examples, consistent cardiac activity (consistent ECG) may enable assumptions to be made regarding the heart activity over multiple cycles, enabling a higher effective frame rate to be achieved. These parameters may change from patient to patient.

In accordance with one or more examples, where, upon segmentation in step 54, the controller 18 determines or detects that the LVOT is positioned peripherally in the probe 16 field of view, or is not fully within the field of view, an operator may be alerted to the fact using a user interface device (e.g. a display or other sensory output means), such that they can adjust the probe positioning to ensure that the LVOT is within the field of view, ideally centrally located within the field of view.

Although in the example described above, use is made of an ultrasound probe, in particular a TEE prove or TTE probe, this is not essential to the inventive concept. Any ultrasound transducer unit able to acquire 3D ultrasound image data and also Doppler ultrasound data (pulsed or continuous wave) of a heart region may be used. This may be an external transducer unit or a semi-invasive probe in accordance with examples.

According to certain embodiments, acquisition of ultrasound data may be performed in ex-vivo fashion (i.e. non-invasively), for example based on use of an ultrasound transducer unit positioned external of the body. In this case, the ultrasound transducer unit may be used for ex-vivo acquisition of ultrasound data of a heart.

In examples, embodiments of the present invention are anticipated for use in clinical environments where an ultrasound probe could be placed in a fixed position, such as with transesophageal ultrasound or transthoracic patch probes, for cardiac monitoring e.g. in an intensive care unit, in an operating room, or in an ambulance.

In accordance with one set of embodiments, the ultrasound imaging system is communicatively coupled with a patient monitoring device and adapted to communicate output information based on the determined stroke volume to the patient monitoring device. The patient monitoring device may include a memory for storing received data. The monitoring device may include a display for displaying acquired information to a user (e.g. clinician). The patient monitoring system may be linked with a patient database containing further information about a given patient which could be displayed in conjunction with the acquired stroke volume information.

The communicative coupling may be wired or wireless. Wireless couplings may be implemented by any wireless communication medium including e.g. Bluetooth, radio frequency communication, NFC, ZigBee, Wi-Fi or any other wireless protocol.

In accordance with one aspect of the invention, there may be provided a patient monitoring system including a patient monitoring device, an ultrasound transducer unit and controller for controlling the transducer unit and determining stroke volume.

As noted above, stroke volume measurements are of particular value in intravenous fluid management, particularly in the case of ventilated patients with need for circulatory assistance and ongoing observation, brought upon for instance by sepsis, brain surgery, cardiac and pulmonary interventions or intensive care.

An ultrasound imaging device according to an embodiment of the present invention may form part of or be provided as part of a wider ultrasound diagnostic imaging system.

Figure 6:
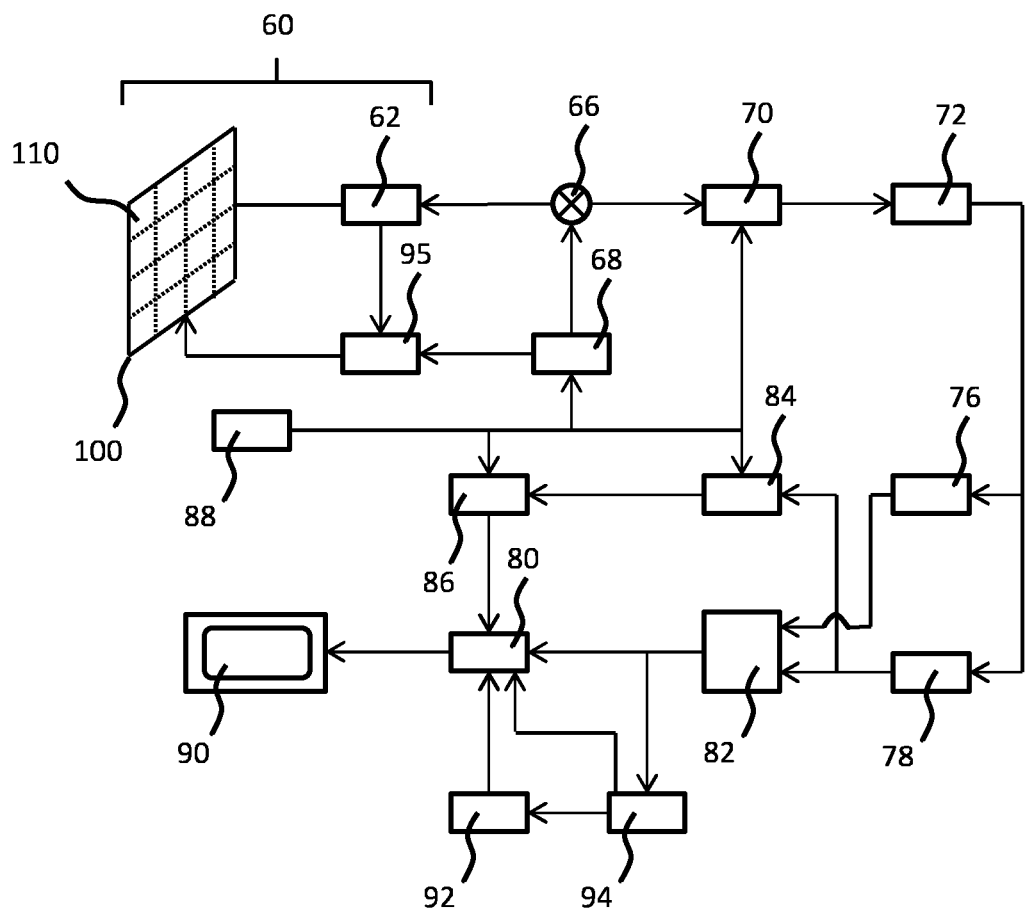
FIG. 6 shows a block diagram of components in an exemplary diagnostic imaging system.

The general operation of an exemplary ultrasound diagnostic imaging system will now be described, with reference to FIG. 6.

The exemplary system comprises an ultrasound transducer unit in the form of an array transducer probe 60 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 62 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479

(Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 62 is coupled by the probe cable to a transmit/receive (T/R) switch 66 which switches between transmission and reception and protects the main beamformer 70 from high energy transmit signals when a microbeamformer is not used and the transducer array is operated directly by the main system beamformer. The transmission of ultrasound beams from the transducer array 60 is directed by a transducer controller 68 coupled to the microbeamformer by the T/R switch 66 and a main transmission beamformer (not shown), which receives input from the user's operation of the user interface or control panel 88.

One of the functions controlled by the transducer controller 68 is the direction in which beams are steered and focused. Beams may be steered straight ahead from (orthogonal to) the transducer array, or at different angles for a wider field of view. The transducer controller 68 can be coupled to control a DC bias control 95 for the CMUT array. The DC bias control 95 sets DC bias voltage(s) that are applied to the CMUT cells.

In the reception channel, partially beamformed signals are produced by the microbeamformer 62 and are coupled to a main receive beamformer 70 where the partially beamformed signals from individual patches of transducers are combined into a fully beamformed signal. For example, the main beamformer 70 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 72. The signal processor 72 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 6 only the receiver beamformers 62, 70 are shown, for simplicity. In the complete system, there will also be a transmission chain with a transmission micro beamformer, and a main transmission beamformer.

The function of the micro beamformer 62 is to provide an initial combination of signals in order to decrease the number of analog signal paths. This is typically performed in the analog domain.

The final beamforming is done in the main beamformer 70 and is typically after digitization.

The transmission and reception channels use the same transducer array 60' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 76 and a Doppler processor 78. The B mode processor 76 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.). The B-mode processor may in examples perform the image segmentation function of the controller 18 described above for identifying location or size information pertaining to the mitral or tricuspid valve and/or the left or right ventricle outflow tract.

The Doppler processor 78 processes temporally distinct signals from tissue movement and blood flow for the detection of the motion of substances such as the flow of blood cells in the image field. The Doppler processor 78 typically includes a wall filter with parameters which may be set to pass and/or reject echoes returned from selected types of materials in the body. The Doppler processor 78 may perform the Doppler processing function(s) of the controller 18 described above. In particular, the Doppler processor 78 may be configured to determine presence of backward directed blood flows through the mitral or tricuspid valve (for identifying regurgitant flow) or blood flows through the left or right ventricle outflow tracts (to determine total blood outflow).

The structural and motion signals produced by the B mode and Doppler processors are coupled to a scan converter 82 and a multi-planar reformatter 94. The scan converter 82 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 92 converts the echo signals of a 3D data set into a projected 3D image as viewed from a given reference point as described in U.S. Pat. No. 6,530,885 (Entrekin et al.).

The 2D or 3D images are coupled from the scan converter 82, multi-planar reformatter 94, and volume renderer 92 to an image processor 80 for further enhancement, buffering and temporary storage for display on an image display 90. In addition to being used for imaging, the blood flow values produced by the Doppler processor 78 and tissue structure information produced by the B mode processor 76 are coupled to a quantification processor 84. The quantification processor produces measures of different flow conditions such as the volume rate of blood flow as well as structural measurements such as the sizes of organs and gestational age. The quantification processor may receive input from the user control panel 88, such as the point in the anatomy of an image where a measurement is to be made. Output data from the quantification processor is coupled to a graphics processor 86 for the reproduction of measurement graphics and values with the image on the display 90, and for audio output from the display device 90.

The graphics processor 86 can also generate graphic overlays for display with the ultrasound images. These graphic overlays can contain standard identifying information such as patient name, date and time of the image, imaging parameters, and the like. For these purposes the graphics processor receives input from the user interface 88, such as patient name.

The user interface is also coupled to the transmit controller 68 to control the generation of ultrasound signals from the transducer array 60' and hence the images produced by the transducer array and the ultrasound system. The transmit control function of the controller 68 is only one of the functions performed. The controller 68 also takes account of the mode of operation (given by the user) and the corresponding required transmitter configuration and band-pass configuration in the receiver analog to digital converter. The controller 68 can be a state machine with fixed states.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Examples in accordance with a further aspect of the invention provide an ultrasound imaging method for determining stroke volume of a heart, the method making use of an ultrasound transducer unit for acquiring ultrasound data of the heart, the method comprising:

performing an initial assessment procedure in which initial ultrasound data is acquired using the transducer unit, and a Doppler processing technique applied to the initial ultrasound data to determine presence or absence of a regurgitant blood flow from a ventricle to an atrium of a heart captured in the initial ultrasound data;

responsive to determining absence of regurgitant flow, implementing a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of a ventricle of the heart at each of said time points, and stroke volume is determined by calculating a change in said volume between said time points;

responsive to determining presence of a regurgitant flow, implementing a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles; and generating output information based on the determined stroke volume.

According to certain embodiments, the ultrasound imaging method may be performed as an ex vivo imaging method (i.e. non-invasively), for example based on use of an ultrasound transducer unit positioned external of the body. In this case the method may hence be an imaging method making use of an ultrasound transducer unit for ex-vivo acquisition of ultrasound data of a heart.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound imaging system for determining stroke volume of a heart, comprising:
   an input for receiving ultrasound data of the heart acquired by an ultrasound transducer unit; and
   a controller adapted to:
      perform an initial assessment procedure in which initial ultrasound data is acquired using the transducer unit, and a Doppler processing technique is applied to the initial ultrasound data to determine presence or absence of a regurgitant blood flow from a ventricle to an atrium of a heart captured in the initial ultrasound data;
      responsive to determining absence of regurgitant flow, implement a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of said ventricle of the heart at each of said time points, and stroke volume is determined by calculating a change in said volume between said time points;
      responsive to determining presence of a regurgitant flow, implement a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles; and
      generate output information based on the determined stroke volume.

2. The ultrasound imaging system as claimed in claim 1, further comprising the ultrasound transducer unit for acquiring ultrasound data of the heart.

3. The ultrasound imaging system as claimed in claim 1, wherein the second imaging procedure comprises identifying a region within a field of view of the ultrasound transducer unit occupied by a ventricle outflow tract of the heart and controlling the transducer unit to acquire ultrasound data representative of only said region.

4. The ultrasound imaging system as claimed in claim 3, wherein said identifying a region comprises:
capturing a first 3D ultrasound image data set representative of the whole field of view of the probe; and
applying an image segmentation technique to the first 3D ultrasound image data set to identify the region occupied by the ventricle outflow tract.

5. The ultrasound imaging system as claimed in claim 4, wherein the segmentation technique is a model-based segmentation technique.

6. The ultrasound imaging system as claimed in claim 4, the second imaging procedure further comprising identifying a size of the ventricle outflow tract.

7. The ultrasound imaging system as claimed in claim 6, wherein the determining of the blood flow out of the ventricle comprises determining a velocity of blood flow through the ventricle outflow tract, and estimating a total blood flow based on said velocity and on the determined size of the ventricle outflow tract.

8. The ultrasound imaging system as claimed in claim 1, wherein the image segmentation procedure of the first imaging procedure is a model-based image segmentation procedure.

9. The ultrasound imaging system as claimed in claim 1 wherein the controller is adapted to:
perform the initial assessment procedure in respect of both a left ventricle and right ventricle of the heart,
responsive to determining absence of regurgitant flow from the left ventricle and/or right ventricle, perform the first imaging procedure in respect of the left ventricle and/or right ventricle; and
responsive to determining presence of regurgitant flow from the left ventricle or right ventricle, perform the second imaging procedure in respect of the left ventricle and/or right ventricle.

10. The ultrasound imaging system as claimed in claim 1, wherein the controller is adapted to perform the initial assessment procedure in respect of either a left ventricle or a right ventricle.

11. The ultrasound imaging system as claimed in claim 10, wherein, in accordance with the first imaging procedure, the controller is adapted to communicate the generated output information and/or the determined indication of variation in stroke volume to an intravenous fluid administration device being in communicative relationship with the controller.

12. The ultrasound imaging system as claimed in claim 1, wherein the first and/or second imaging procedure comprises:
acquiring ultrasound data corresponding to multiple heart cycles;
determining a stroke volume for each heart cycle; and
further determining an indication of a variation in stroke volume between heart cycles.

13. The ultrasound imaging system as claimed in claim 1 wherein the controller is adapted to receive an electrocardiogram signal input representative of the cardiac cycle, the signal input used for synchronizing ultrasound data acquisition with the cardiac cycle.

14. The ultrasound imaging system as claimed in claim 1, wherein the system further comprises a display unit, the controller being adapted to control the display unit to display a visual representation of the output information.

15. The ultrasound imaging system as claimed in claim 1, wherein the controller is communicatively coupled with a patient monitoring device and adapted to communicate the output information to the patient monitoring device.

16. The ultrasound imaging system as claimed in claim 1, wherein the output information is indicative of a cardiac output, the cardiac output determined based on the determined stroke volume and a heart rate for the heart.

17. The ultrasound imaging system as claimed in claim 1, wherein the ultrasound transducer unit is a transesophageal echocardiography probe or a transthoracic echocardiography probe.

18. A patient monitoring system, comprising:
a patient monitoring device;
an input for receiving ultrasound data of a heart from an ultrasound transducer unit, which is operatively coupled with the patient monitoring device; and
a controller for controlling the ultrasound transducer unit and determining stroke volume of said heart, the controller adapted to:
perform an initial assessment procedure in which initial ultrasound data is acquired using the transducer unit, and a Doppler processing technique is applied to the initial ultrasound data to determine presence or absence of a regurgitant blood flow from a ventricle to an atrium of a heart captured in the initial ultrasound data;
responsive to determining absence of regurgitant flow, implement a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of said ventricle of the heart at each of said time points, and stroke volume is determined by calculating a change in said volume between said time points;
responsive to determining presence of a regurgitant flow, implement a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles.

19. The patient monitoring system according to claim 18, further comprising the ultrasound transducer unit for acquiring ultrasound data of the heart, wherein said transducer unit is operatively coupled with the patient monitoring device.

20. An ultrasound imaging method for determining stroke volume of a heart, the method comprising:
performing an initial assessment procedure in which initial ultrasound data is acquired using an ultrasound transducer unit, and a Doppler processing technique applied to the initial ultrasound data to determine presence or absence of a regurgitant blood flow from a ventricle to an atrium of a heart captured in the initial ultrasound data;

responsive to determining absence of regurgitant flow, implementing a first imaging procedure in which: the transducer unit is controlled to acquire 3D ultrasound image data at only an end-systolic time point and end-diastolic time point of a cardiac cycle of the heart, an image segmentation procedure is applied to the 3D ultrasound image data to determine a volume of a ventricle of the heart at each of said time points, and stroke volume is determined by calculating a change in said volume between said time points;

responsive to determining presence of a regurgitant flow, implementing a second imaging procedure in which stroke volume is determined by: controlling the transducer unit to acquire ultrasound data across a full duration of one or more cardiac cycles, and applying a further Doppler processing technique to said ultrasound data to identify a total blood flow out of said ventricle of the heart during each of the one or more cardiac cycles; and generating output information based on the determined stroke volume.

\* \* \* \* \*